US00PP31170P2

(12) United States Plant Patent
Hansen

(10) Patent No.: US PP31,170 P2
(45) Date of Patent: Dec. 3, 2019

(54) ***PHLOX* PLANT NAMED 'PINK MINUET'**

(50) Latin Name: ***Phlox* hybrid**
Varietal Denomination: Pink Minuet

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,915

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ..... A01H 5/02; A01H 6/70
See application file for complete search history.

*Primary Examiner* — Annette H Para

(57) ABSTRACT

A unique cultivar of Hybrid Spring Phlox named *Phlox* 'Pink Minuet' characterized by multi-stemmed, heavily branched, compact, mounded, winter-hardy habit, producing short, bright glossy-green, awl-shaped leaves. Numerous flowers begin in late-April for three weeks on moderately-branched peduncles, nearly completely covering the plant in peak season. Flowers sporadically for four or five weeks later in the season. Petals are rosy-pink with two small striae marks in the center eye of dark-purple. Petal apices are shallowly notched. Foliage stays clean and resists mildew, and the new plant is especially suitable as a potted plant and in the garden as a specimen or en masse.

1 Drawing Sheet

Botanical classification: *Phlox* hybrid.
Variety denomination: 'Pink Minuet'.

STATEMENT REGARDING PRIOR DISCLOSURES UNDER 37 CFR 1.77(b)(6)

The first public disclosure of the claimed plant, was in the form of a photograph and brief description on a website operated by Walters Gardens, Inc. on Feb. 1, 2018. The claimed plant was first sold on Jul. 10, 2018 by Walters Gardens, Inc., who obtained the plant and all information relating thereto, from the inventor. No plants of *Phlox* 'Pink Minuet' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Pink Minuet' and will be referred to hereafter by its cultivar name, 'Pink Minuet', or the "new plant". The new plant was hybridized by the inventor at a wholesale perennial nursery in Zeeland, Mich. on Jan. 31, 2014 as a cross between an unnamed, proprietary selection of *Phlox procumbens* (not patented) as the female parent times *Phlox bifida* 'Top Notch' (not patented) as the male parent. The new plant passed initial evaluation on the spring of 2016 and was assigned the breeder code 14-134-1 through the remaining evaluation process. 'Pink Minuet' was first asexually propagated by stem cuttings in the greenhouses at the same nursery in Zeeland, Mich. in the summer of 2016. The unique characteristics of the new plant have been found to be reproducible and stable in successive generations of asexually propagated and the resultant plants have been found to be identical to the original selection.

BRIEF SUMMARY OF THE PLANT

*Phlox* 'Pink Minuet' is unique from all other Hybrid Spring Phlox known to the inventor. The nearest comparison plants known to the inventor include: 'Magenta Sprite' U.S. Plant patent application Ser. No. 16/350,550, 'Purple Sprite' U.S. Plant patent application Ser. No. 16/350,524, 'Rose Sprite' U.S. Plant patent application Ser. No. 16/350,549 and 'PPPHL0604' U.S. Plant Pat. No. 23,703. 'Magenta Sprite' has flowers of magenta-pink, the habit is slightly taller and tend not to repeat flowering later in the season. 'Purple Sprite' has flowers of bright purple, the habit is slightly taller and tend not to repeat flowering later in the season. 'Rose Sprite' has flowers of rose-pink, the habit is slightly taller and tend not to repeat flowering later in the season. 'PPPHL0604' has flowers that have a lighter near-white eye. The female parent, 'Purple Beauty' has a shorter habit and smaller flowers that are a slightly different hue. The male parent, *Phlox bifida* 'Top Notch', has flowers that are lavender with deeply cleft petal apices.

*Phlox* 'Pink Minuet' differs from and all other phlox known to the inventor in the following repeatedly observed traits in combination:

1. Plants of compact, mounded habit, producing short, clean, glossy, dark-green, linear leaves;
2. Multiple heavily-branched stems produce moderately branched panicles;
3. Numerous flowers beginning in late-April and continuing for about three weeks nearly completely covering plant at peak flowering;

4. Flowering continues for about four of five weeks after a short rest of about three weeks;
5. Flowers are rosy-pink with small dark-purple eye;

BRIEF DESCRIPTION OF THE DRAWINGS

The photographs of the new plant demonstrate the unique traits of *Phlox* 'Pink Minuet' and the overall appearance of the plant at three-years old growing in a full-sun trial bed in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
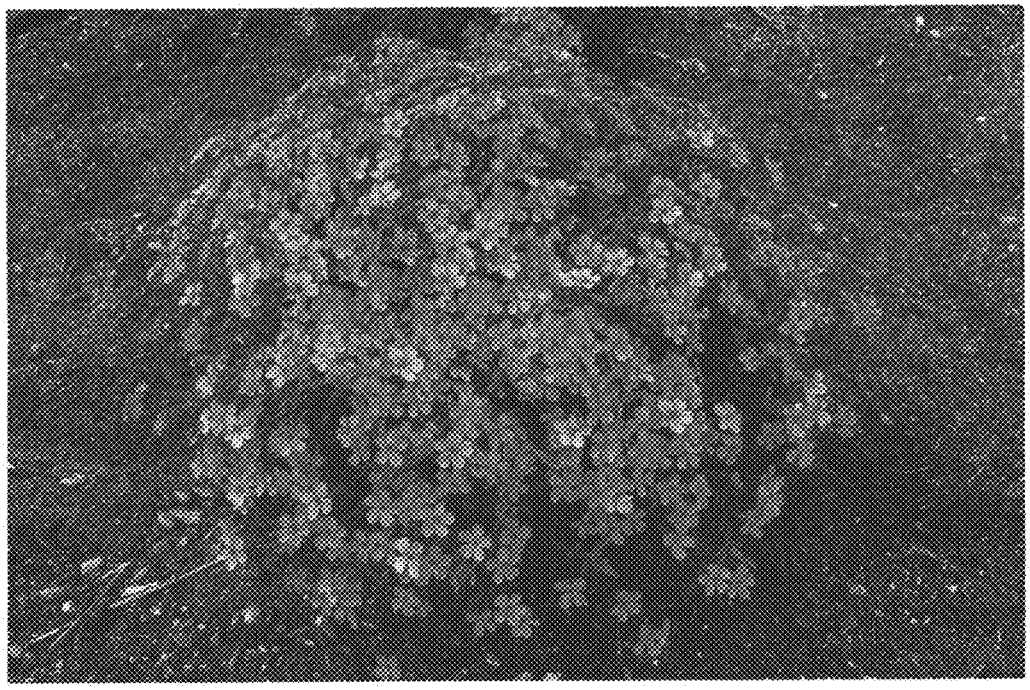
FIG. 1 shows the new plant in peak flower in the landscape.
Figure 2:
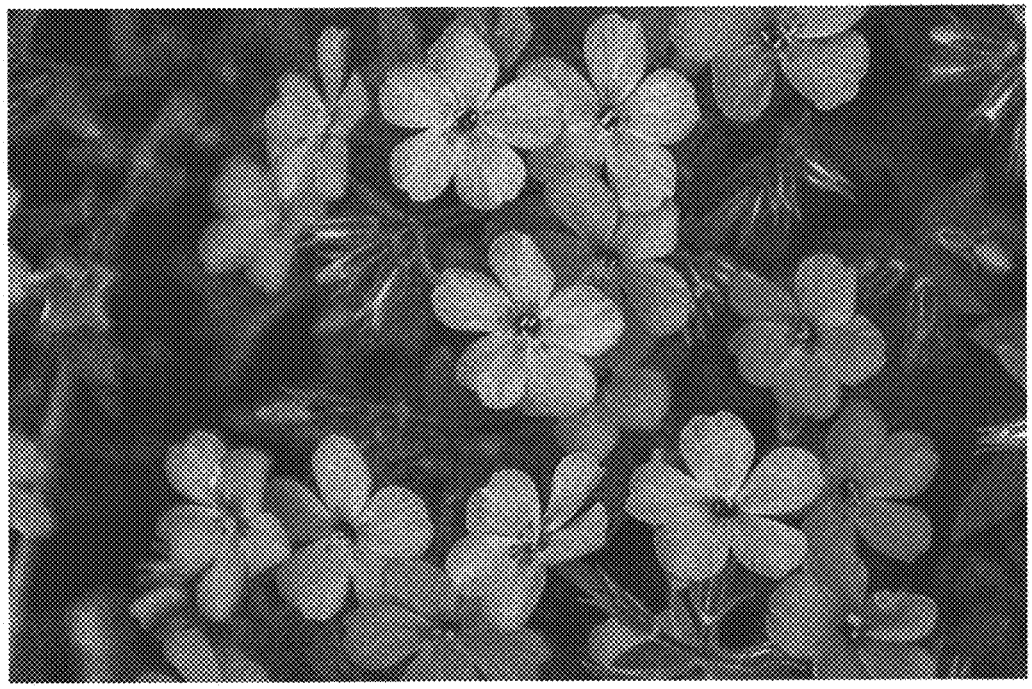
FIG. 2 shows a close-up of the flowers and buds.

The following descriptions and color references are based on the 2015 edition of The Royal Horticultural Society Colour Chart except where common dictionary terms are used. *Phlox* 'Pink Minuet' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid.

Parentage: female or seed parent is an unnamed proprietary selection of *Phlox procumbens*, male or pollen parent is *Phlox bifida* 'Top Notch'.

Plant habit: winter-hardy, compact, densely-mounded, highly-branched, herbaceous perennial; producing about 50 to 75 stiff, highly-branched stems; foliage 13.5 cm tall and 34.0 cm wide, average 130 cm tall and 35.0 cm wide; flowering to 18.0 cm tall and 38.0 cm wide.

Propagation: stem cuttings; rooting in about 3 weeks.

Time to produce finished crop in 3.8 liter pots: about 8 to 12 weeks; moderately vigorous.

Root: fibrous and freely branching; color creamy white to tan depending on soil type.

Leaves: simple; opposite proximally, whorled distally; linear; apex apiculate; base truncate, clasping; margin entire, micro-ciliolate; lustrous and glabrous both adaxial and abaxial; about 15.0 mm long by about 3.5 mm wide.

Leaf color: adaxial expanding between RHS 143A and RHS 144A, abaxial expanding nearest RHS 144A; mature adaxial nearest RHS 137B and mature abaxial nearest RHS 138B.

Foliage fragrance: none detected.

Veins: pinnate; not conspicuous adaxial and abaxial.

Vein color: same color as surround leaf.

Petiole: leaves sessile.

Stems: cylindrical; flexible; strong; wiry; to 1.5 mm diameter and branching at nearly every node; strong; upright; covered in leaves distally; about 15.0 cm long and 1.5 mm diameter at base.

Stem color: variable; nearest RHS 187C in high light and nearest RHS 146D in low indirect light.

Nodes: proximally about 9.0 mm apart; distally less than 1.0 mm apart; average about 1.7 mm apart.

Node color: same as surrounding stem.

Inflorescence: to 5.5 cm long and 4.0 cm wide; with up to 7 flowers per inflorescence.

Flowers: perfect; salverform; mostly flat faced; about 18.0 mm across the flat face and 16.0 mm long; with fused corolla tube about 14.0 mm long and 2.5 mm diameter near face; attitude upright to outwardly.

Flower longevity: about 5 days on plant; self-cleaning.

Flower fragrance: not detected.

Buds one to two days prior to opening: narrowly oblanceolate, to narrowly clavate; acute apex with petals implicate; about 15.0 mm long, 7.5 mm long in terminal bulb portion and 13.5 mm long in tube; tube to 2.0 mm diameter; bulb to 3.5 mm diameter.

Bud color: nearest RHS 70B in distal bulb portion, exposed tube nearest RHS 83B.

Petals; five; glabrous; obdeltoid; cleft blade and claw base fused into tube; apex rounded, emarginate, notched between 0.5 and 1.0 mm deep; margin entire; blades rarely imbricate; glabrous adaxial and abaxial.

Petal size: blade about 8.0 mm long and 7.0 mm wide near center; tube about 13.0 mm long and 2.0 mm diameter.

Petal color:

Adaxial: blade nearest RHS NN74B with two 1.0 mm striae near eye nearest blend of RHS 71A and RHS N79C, tube nearest RHS 69B, basal tube 2.0 mm nearest RHS 145D.

Abaxial; blade between RHS NN74B and NN74C, basal tube 2.0 mm nearest RHS 145D, distal tube nearest RHS N79D; with 1.0 mm ring between tube and bulb nearest RHS 83A.

Androecium: typically five.

Filaments: typically five, adnate to inner corolla at various heights; about 1.0 mm and 0.1 mm in diameter; color nearest RHS NN155D.

Anther: oblong elliptic; dorsifixed; oblong, about 2.0 mm long by 1.0 mm wide; color nearest RHS 17B.

Pollen: nearly microscopic, spherical; color nearest RHS 23A.

Gynoecium: one pistil per flower; 15.0 mm long.

Style: cylindrical; about 13.0 mm long and 0.2 mm diameter when flower is mature; persistent after flower abscission; color nearest RHS 157D.

Stigma: trifid in proximal 1.0 mm, about 0.2 mm diameter; nearest RHS 4B.

Ovary: inferior; globose, rounded to slightly obtuse apex and truncate base; about 1.2 mm long and 1.0 mm diameter; color nearest RHS 144A.

Calyx: campanulate; about 7.0 mm long and 4.0 mm across at apex.

Sepals; five; linear to lanceolate; narrowly acute apex, fused in basal 3.0 mm; margin entire; puberulent abaxial, glabrous and lustrous adaxial; individually about 7.0 mm long and 1.0 mm wide at fusion.

Sepal color: adaxial nearest RHS 187A toward apex and lightening to nearest RHS 147C in base, abaxial nearest RHS 138A with strong to light blush of nearest RHS 187A.

Peduncle: finely puberulent; strong, flexible; upright to outwardly, cylindrical; about 1.5 mm diameter at base and 4.5 cm long.

Peduncle color: nearest RHS 146C blushed with RHS 187A.

Pedicle: cylindrical; finely puberulent; flexible; upright to outwardly; to about 4.0 mm long and 8.0 mm diameter.

Pedicle color: nearest RHS 187A.

Fruit and seeds: not yet been observed.

Hardiness and culture: the new plant grows best with full sun, plenty of moisture and adequate drainage; hardy to at least from USDA zone 4 through 8.

Disease and pest resistance: *Phlox* 'Pink Minuet' demonstrates excellent powdery mildew resistance under conditions that would normally show symptoms.

I claim:

1. A new and distinct cultivar of *Phlox* plant named 'Pink Minuet' as herein described and illustrated.

* * * * *